_(12)_ United States Patent
Wang et al.

(10) Patent No.: US 7,485,754 B2
(45) Date of Patent: Feb. 3, 2009

(54) EFFICIENT METHOD FOR PREPARING 3-ARYLOXY-3-ARYLPROPYLAMINES AND THEIR OPTICAL STEREOISOMERS

(75) Inventors: Zhi-Xian Wang, Brantford (CA); Mohammed Abdul Raheem, Brantford (CA); Gamini Weeratunga, Brantford (CA); Bhaskar Reddy Guntoori, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 89 days.

(21) Appl. No.: 11/176,361

(22) Filed: Jul. 8, 2005

(65) Prior Publication Data

US 2007/0010678 A1    Jan. 11, 2007

(51) Int. Cl.
*C07C 215/08* (2006.01)
(52) U.S. Cl. ..................................... 564/355
(58) Field of Classification Search .................. 564/355
See application file for complete search history.

(56) References Cited

U.S. PATENT DOCUMENTS

| | | | |
|---|---|---|---|
| 4,314,081 | A | 2/1982 | Molloy et al. |
| 4,777,291 | A | 10/1988 | Misner |
| 4,868,344 | A | 9/1989 | Brown |
| 5,068,432 | A | 11/1991 | Brown |
| 5,847,214 | A | 12/1998 | Arosio et al. |
| 6,008,412 | A | 12/1999 | Ratz |
| 6,541,668 | B1 | 4/2003 | Kjell et al. |
| 6,686,505 | B2 | 2/2004 | Watanabe et al. |

FOREIGN PATENT DOCUMENTS

| | | |
|---|---|---|
| EP | 0 052 492 | 2/1984 |
| WO | WO 94/00416 | 1/1994 |
| WO | WO 00/58262 | 10/2000 |
| WO | WO 02/057475 | 7/2002 |

OTHER PUBLICATIONS

Berge et al. J. Pharmaceutical Sciences 1977, 669(1), 1-18.*
Sakuraba et al. Chemical & Pharmaceutical Bulletin 1995, 43(5), 748-753.*
Kamal et al. Tetrahedron Letters 2003, 44(25), 4783-4787.*
Tomoxetin Hydrochloride, Drugs of the Future, 11(2), pp. 134-135 (1986).
D. W. Robertson et al., Absolute Configurations and Pharmacological Activities of the Optical Isomers of Fluoxetine . . . , J. Med. Chem., 31(7), pp. 1412-1417 (1988).
E. J. Corey and G. A. Reichard, Enantioselective and Proactical Syntheses of R- and S-Fluoxetines, Tetrahedron Letters, 30(39), pp. 5207-5210 (1989).
P. N. Devine et al., Stereoselective Synthesis of 2-Aryloxy Esters: An Asymmetric Approach to Fluoxetine, Tomoxetine and Nisoxetine, Tetrahedron, 53(2), pp. 6739-6746 (1997).
T. M. Koening and D. Mitchell, A Convenient Method for Preparing Enantiomerically Pure Norfluoxetine, Fluoxetine and Tomoxetine, Tetrahedron Letters, 35(9), pp. 1339-1342 (1994).
M. Srebnik et al., Chiral Synthesis via Organoboranes. 18. Selective Reductions. 43. Diisopinocampheylchloroborane . . . , J. Organic Chemistry, 53(13), pp. 2916-2920 (1988).
Y. Gao and K. B. Sharpless, Asymmetric Synthesis of Both Enantiomers of Tomoxetine and Fluoxetine. Selective Reduction of . . . , J. Org. Chem., 53(17), pp. 4081-4084 (1988).
J. Deeter et al., Asymmetric Synthesis and Absolute Stereochemistry of LY248686, Tetrahedron Letters, 31(49), pp. 7101-7104 (1990).
M. P. Schneider and U. Goergens, An efficient route to enantiomerically pure antidepressants: Tomoxetine, Nisoxetine . . . , Tetrahedron: Asymmetry, 3(4), pp. 525-528 (1992).
M. Wolter et al., Copper-Catalyzed Coupling of Aryl Iodides with Aliphatic Alcohols, Organic Letters 4(6), pp. 973-976 (2002).
G. E. Job and S. L. Buchwald, Copper-Catalyzed Arylation of B-Amino Alcohols, Organic Letters, 4(21), pp. 3703-3706 (2002).
R. N. Salvatore et al., Synthesis of secondary amines, Tetrahedron, 57, pp. 7785-7811 (2001).
M. B. Smith and J. March, Advanced Organic Chemistry, fifth edition, John Wiley & Sons, Inc., pp. 499-502 (2001).
V. Ratovelomanana-Vidal et al., Enantioselective Hydrogenation of B-Keto Esters using Chiral Diphosphine-Ruthenium . . . , Adv. Synth. Catal. 345(1&2), pp. 261-274 (2003).
I. S. Ali and A. Sudalai, Pd-catalyzed kinetic resolution of benzylic alcohols: a practical synthesis of (R)-tomoxetine and . . . , Tetrahedron Letters, 43, pp. 5435-5436 (2002).
A. Kamal et al., Chemoenzymatic synthesis2 of both enantiomers of fluoxetine, tomoxetine and nisoxetine . . . , Tetrahedron: Asymmetry, 13, pp. 2039-2051 (2002).
D. Mitchell and T. M. Koenig, Synthesis of R- and S- Fluoxetine, Norfluoxetine and Related Compounds from Styrene Oxide, Synthetic Communications, 25(8), pp. 1231-1238 (1995).
A. Kumar et al., A novel chemoenzymatic enantioselective synthesis of some clinically effective CNS drugs and related compounds, Indian J. Chem., 31B, pp. 803-809 (1992).
A. Klapars et al., A General and Efficient Copper Catalyst for the Amidation of Aryl Halides, J. American Chemical Society, 124(25), pp. 7421-7428 (2002).

\* cited by examiner

*Primary Examiner*—Kamal A Saeed
*Assistant Examiner*—Jason Nolan
(74) *Attorney, Agent, or Firm*—Graham J. K. McKinnon; Apotex Inc.

(57) ABSTRACT

Provided is an efficient method for the preparation of 3-aryloxy-3-arylpropylamines, their optical stereoisomers, and pharmaceutically acceptable salts thereof. The process allows for the isolation of 3-aryloxy-3-arylpropylamines in high yield and purity. The present invention further relates to a process for producing fluoxetine, tomoxetine, norfluoxetine, duloxetine, nisoxetine, and their optically enriched (R)- and (S)-enantiomers.

49 Claims, No Drawings

EFFICIENT METHOD FOR PREPARING 3-ARYLOXY-3-ARYLPROPYLAMINES AND THEIR OPTICAL STEREOISOMERS

FIELD OF THE INVENTION

The present invention relates to a process for producing 3-aryloxy-3-arylpropylamines of formula 1, including fluoxetine, tomoxetine, norfluoxetine, duloxetine, nisoxetine, and their optically enriched (R)- and (S)-enantiomers.

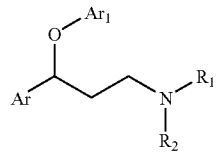

1

Fluoxetine: Ar = Ph, $Ar_1$ = 4-trifluoromethylphenyl, $R_1$ = Me, $R_2$ = H
Tomoxetine: Ar = Ph, $Ar_1$ = 2-methylphenyl, $R_1$ = Me, $R_2$ = H
Norfluoxetine: Ar = Ph, $Ar_1$ = 4-trifluoromethylphenyl, $R_1$ = $R_2$ = H
Nisoextine: Ar = Ph, $Ar_1$ = 2-methoxyphenyl, $R_1$ = Me, $R_2$ = H
Duloxetine: Ar = 2-thienyl, $Ar_1$ = 1-naphthyl, $R_1$ = Me, $R_2$ = H

BACKGROUND OF THE INVENTION

The selective serotonin reuptake inhibitors and norepinephrine reuptake inhibitor class of antidepressants, which have the 3-aryloxy-3-arylpropylamine sub-structure, e.g. fluoxetine, tomoxetine, nisoxetine, norfluoxetine, and duloxetine, are among the most important pharmaceuticals for the treatment of psychiatric disorders such as anxiety and clinical depression (*Drugs of the Future*, 11, 134 (1986)). In addition, several members of this class have shown promise for the treatment of alcoholism, chronic pain and eating disorders such as obesity and bulimia (*J. Med. Chem.* 31, 1412 (1988)). Fluoxetine hydrochloride is marketed as its racemate (Prozac™, Eli Lilly Co.), but recently interest has been shown for marketing the more active (R)-enantiomer as an "Improved Chemical Entity" version of the drug. Tomoxetine was the first norepinephrine reuptake inhibiting antidepressant without strong affinity for α- or β-adrenergic receptor. The (R)-enantiomer, also called atomoxetine, is marketed as its hydrochloride salt under the name of Strattera™ and is purportedly ninefold more potent relative to the (S)-enantiomer.

There are several general synthetic methods reported in the prior art for the synthesis of 3-aryloxy-3-arylpropylamines 1 and their optically pure enantiomers. For example, U.S. Pat. No. 4,314,081 disclosed the racemic preparation of compounds of formula 1 via alkylation of substituted phenols with benzyl halide intermediates followed by further chemical elaboration. *Tetrahedron Lett.* 30, 5207-5210 (1989) disclosed the preparation of (R)-fluoxetine by the nucleophilic aromatic displacement reaction of (R)—N-methyl-3-hydroxy-3-phenylpropylamine with p-chlorobenzotrifluoride. A stereoselective route for the preparation of (S)-tomoxetine was disclosed in *Tetrahedron*, 53, 6739-6746 (1997), which utilized as a key step the coupling of lithiated o-cresol with a chiral iodoester to furnish an aryl ether intermediate. U.S. Pat. No. 5,068,432 disclosed the preparation of optically pure fluoxetine and tomoxetine using a Mitsunobu reaction for the coupling step.

More specifically, etherification by the nucleophilic aromatic displacement of 3-hydroxy-3-arylpropylamines 2 with aryl halides represents the most straightforward method of preparation.

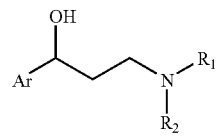

2

For example, the reaction of N-methyl-3-hydroxy-3-phenylpropylamine with 4-trifluoromethyl-1-chlorobenzene in the presence of a strong base in dimethylsulfoxide (WO 94/00416), 1,3-dimethyl-2-imidazolidinone or N-methylpyrrolidinone (U.S. Pat. No. 5,847,214) have been reported to give N-methyl-(4-trifluoromethylphenoxy)-3-phenylpropylamine (fluoxetine). In addition, the reaction of an unactivated substrate, 2-fluorotoluene, with the alkoxide of (S)—N-methyl-3-phenyl-3-hydroxypropylamine in dimethylsulfoxide gave a modest yield and racemization (*Tetrahedron Lett.* 35, 1339-1342 (1994)). U.S. Pat. No. 6,541,668 disclosed that N-methyl-3-(2-methylphenoxy)-3-phenylpropylamine (tomoxetine) can be prepared by coupling 2-fluorotoluene with N-methyl-3-phenyl-3-hydroxypropylamine in 1,3-dimethyl-2-imidazolidinone in the presence of a strong base, such as potassium t-butoxide at about 110° C. These methods partially resolve some of the preparative problems associated with 3-aryloxy-3-arylpropylamines; however, these methods still suffer from various deficiencies including the use of expensive and undesired solvents, harsh reaction conditions (e.g., high temperature), the need for strong bases, and the loss of chirality when unactivated aryl halides and optically pure intermediates are used. Therefore, development of a process using a common solvent, less expensive reagents and mild reaction conditions is desired.

The stereospecific synthesis of 3-aryloxy-arylpropylamines is known in the art. In many of these methods, the asymmetry is introduced by utilizing enantiomers of 3-hydroxy-3-arylpropylamines, prepared by either stereospecific reduction of a ketone precursor or by resolution of the alcohol [*J. Org. Chem.* 53, 2916-2920 (1988); *Tetrahedron Lett.* 30, 5207-5210 (1989); U.S. Pat. No. 4,868,344; *J. Org. Chem.* 53, 4081-4084 (1988); and *Tetrahedron Lett.* 31, 7101 (1990)]. In general, when employing a specific enantiomer of the alcohol, the 3-aryloxy substituent is introduced by either the Mitsunobu reaction using a phenol or by nucleophilic aromatic displacement of the alkoxide on an aryl halide. However, due to the expense and difficulty of the Mitsunobu reaction at large scale, a commercial process that uses the nucleophilic aromatic displacement route is preferred.

Unfortunately, nucleophilic aromatic displacement reactions with 3-hydroxy-3-arylpropylamines normally require a strong base such as sodium hydride which may lead to racemization of the stereochemical center (*J. Org. Chem.* 53, 4081-4084 (1988); *Tetrahedron Asymmetry*, 3, 525-528 (1992); *Tetrahedron Lett.* 35, 1339-1342 (1994)). Also, low to modest yields are obtained when unactivated aryl halides are used. For example, the reaction of 2-fluorotoluene with the alkoxide of (S)—N-methyl-3-phenyl-3-hydroxypropylamine gives modest chemical yields of tomoxetine and epimerization of the chiral center was observed (*Tetrahedron Lett.* 35, 1339-1342 (1994)). For this reason, there are no stereospecific methods for the preparation of optically pure (R)—N-methyl-3-phenyl-3-(2-methylphenoxy)propylamine (Atomoxetine) and its enantiomer, (S)—N-methyl-3-phenyl-3-(2-methylphenoxy)propylamine by the direct aromatic displacement reaction of optically pure (R)- and (S)-3-hydroxy- 3-phenylpropylamine with aryl halides. Therefore, a general method of producing optically active 3-aryloxy-3-arylpropylamines from optically active 3-hydroxy-3-arylpropylamines using a stereospecific aromatic displacement reaction, especially for the preparation of optically enriched (R)—N-methyl-3-phenyl-3-(2-methylphenoxy)propylamine (Atomoxetine) and its enantiomer, (S)—N-methyl-3-phenyl-3-(2-methylphenoxy)propylamine, is still attractive.

Methods of producing alkyl aryl ethers employing the traditional Williamson ether synthesis include direct nucleophilic substitution and the Cu(I)-catalyzed cross-coupling of alkoxides with aryl halides. However, these methods are limited in that they typically require activated aryl halides, large excesses of alkoxides, high reaction temperature and undesirable solvents. Recently, the palladium-catalyzed cross-coupling reaction of aryl halides with alcohols has been reported as an alternative method for the formation of the aryl-oxygen bond. Although this avoids many of the stated above limitations, the intermolecular reaction has been most successful using activated aryl halides.

A mild method for the etherification of aryl iodides and aliphatic alcohols that does not require the use of alkoxide bases was described in a recent article (*Org. Lett.* 4, 973-976 (2002)). The reaction was carried out in the presence of a catalytic amount of copper iodide and about 20 mole percent of the expensive (100-g=$309.50) and relatively toxic 1,10-phenanthroline catalyst. Also, a method of O-arylation of β-amino alcohols catalyzed by Cu(I) catalyst has also been reported (*Org. Lett.* 4, 3703-3706 (2002)), however all the examples in this article were for β-amino alcohol substrates and the authors report the complete lack of reactivity of simple alcohols under their conditions. From an industrial perspective, these copper-mediated reactions are attractive since copper reagents are relatively inexpensive and the reaction conditions are mild; however, the requirement of the toxic 1,10-phenanthroline as a catalyst is unfortunate from a pharmaceutical perspective.

With respect to the intermediates, preparations of 3-hydroxy-3-arylpropylamines and their optically pure enantiomers have been disclosed in the prior art. Among them, the most straightforward method is treatment of the hydroxy compound of formula 3 with the amine of formula 4 (Scheme 1), wherein LG is a leaving group.

Scheme 1

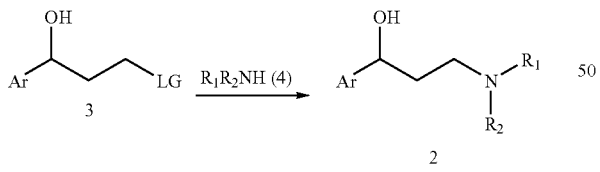

However, although the conversion appears deceptively simple, it is well known that the synthetic value of this method is limited when one of $R_1$ and $R_2$ is hydrogen due to the concomitant over-alkylation, which results in mixtures of primary, secondary and tertiary amines, as well as quaternary ammonium salts (*Tetrahedron*, 57, 7785-7811 (2001)). This deficiency is compounded by the fact that compounds of formula 2 are difficult to purify since they are usually isolated as a viscous oil or low melting solid. Thus, in addition to the long-felt need for an efficient and cost-effective synthetic method for preparation of 3-aryloxy-3-propylamines, it is furthermore desirable to develop an efficient and cost-effective process to prepare compounds of formula 2 from compounds of formula 3 and isolate the compounds of formula 2 in pure form.

SUMMARY AND DETAILED DESCRIPTION OF THE INVENTION

According to one aspect of the invention, a process is provided for the preparation of 3-hydroxy-3-arylpropylamines of formula 2,

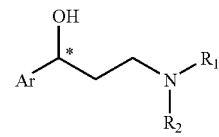

wherein Ar is an aryl group, of which phenyl and 2-thienyl are preferred; $R_1$ and $R_2$ individually represent hydrogen, C1-C10 alkyl, phenyl, and benzyl groups; the carbon center marked with "*" can be racemic or enantiomerically enriched (R)— or (S)— configuration; and pharmaceutically acceptable addition salts thereof comprising the steps of:

(1) reacting compounds of formula 3,

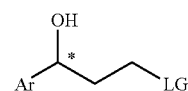

wherein Ar and "*" are as defined above; LG is a leaving group selected from halogens such as chloro, bromo, and iodo and sulfonate esters such as mesylate and p-tosylate, with an amine of formula $R_1R_2NH$ (4), wherein $R_1$ and $R_2$ are as defined above, and purifying and isolating the coupled product as its oxalic acid salt of formula 5,

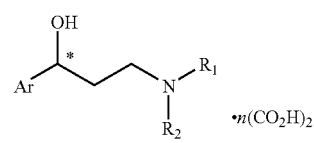

wherein Ar, $R_1$, $R_2$, and "*" are as defined above and n is 0.5 or 1; and (2) treating the salt 5 with a base to produce 3-hydroxy-3-arylpropylamines of formula 2,

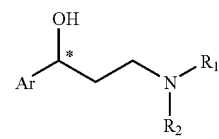

wherein Ar, $R_1$, $R_2$, and "*" are as defined above.

The N-alkylation of amines of formula 4 with compounds of formula 3 to provide crude 3-hydroxy-3-arylpropylamines 2 can be carried out using methods previously described in the art, for example, the methods disclosed in: *Advanced Organic Chemistry, fifth edition*, by J. March, John Wiley & Sons, Inc. (2001), pp 499-502; *Tetrahedron*, 57, 7785-7811 (2001); *Tetrahedron Asymmetry*, 3, 525-528 (1992); *Tetrahedron Lett.* 30, 5207-5210 (1989); and *J. Org. Chem.* 53, 2916-2920 (1988).

Surprisingly, we have discovered that 3-hydroxy-3-arylpropylamines 2 can be isolated in high yield and purity as their oxalate salts. This process provides a commercially practical preparation of 3-hydroxy-3-arypropylamines 2 via the reaction of compounds of formula 3 with amines of formula 4 followed by isolation and purification of the coupled product as their oxalate salt 5 using readily available and inexpensive oxalic acid as the acid source. Salts of formula 5 can then be readily free-based to provide the useful intermediates of formula 2. There are no literature reports for the use of simple organic or inorganic acids to purify compounds of formula 2.

According to an aspect of the present invention, the 3-hydroxy-3-arylpropylamine product is treated with oxalic acid in an organic solvent or mixture of solvents, to furnish 3-hydroxy-3-arylpropylamine oxalate salts of formula 5. The amount of oxalic acid ranges from 0.3 to 5 equivalents relative to 3, and preferably 0.5 to 1.0 eq. The suitable solvents include alcohols, alkyl ethers, alkyl esters, ketones, aromatic and aliphatic hydrocarbons, and halogenated hydrocarbons. Examples of suitable alcohols include methanol, ethanol, propanols, and butanols; examples of suitable alkyl ethers include diethyl ether, methyl t-butyl ether, diisopropyl ether, butyl ether; examples of suitable alkyl esters include ethyl acetate; examples of suitable aliphatic hydrocarbons include hexanes and heptanes; examples of suitable aromatic hydrocarbons include toluene and xylenes; examples of suitable halogenated hydrocarbons include dichloromethane and dichloroethane; examples of suitable ketones include acetone, methyl ethyl ketone, methyl isobutyl ketone, and mixtures thereof.

The regeneration of 3-hydroxy-3-arylpropylamines of formula 2 from their oxalic acid salts of formula 5 may be effected by treatment of the salt with a base or by a basic ion-exchange resin. Suitable bases include organic and inorganic bases, of which sodium hydroxide, potassium hydroxide, lithium hydroxide, sodium carbonate, potassium carbonate, lithium carbonate, ammonia, and triethylamine are preferred.

According to another aspect of the present invention, a process for the preparation of 3-aryloxy-3-arylpropylamines of the formula 1,

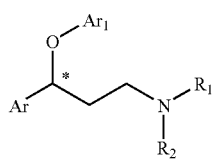

1 is provided wherein Ar is an aryl group, of which phenyl and 2-thienyl are preferred; $Ar_1$ is an aryl group, of which 1-naphthyl, 2-methylphenyl, 2-methoxyphenyl, and 4-trifluoromethylphenyl are preferred; $R_1$ and $R_2$ individually represent hydrogen, C1-C10 alkyl, phenyl, and benzyl groups; the carbon center marked with "*" can be racemic or enantiomerically enriched (R)- or (S)— configuration; including fluoxetine, tomoxetine, nisoxetine, norfluoxetine, duloxetine and their optically enriched (R)- and (S)-enantiomers, and pharmaceutically acceptable addition salts thereof comprising the steps of:

(1) reacting compounds of formula 2,

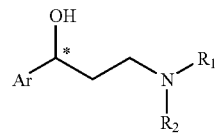

2 wherein Ar, $R_1$, $R_2$, and "*" are as defined above with an aryl halide of formula $Ar_1X$ (6), wherein $Ar_1$ is as defined above; and X is selected from halogens such as fluoro, chloro, bromo, and iodo, of which iodo is preferred, in the presence of a suitable catalyst and a base or mixture of bases to produce 3-aryloxy-3-arylpropylamines of formula 1; and 2) optional formation of an acid addition salt using a pharmaceutically acceptable acid.

The 3-aryloxy-3-arylpropylamines described herein form pharmaceutically acceptable acid addition salts with a wide variety of organic and inorganic acids.

Previously, the general synthesis of 3-aryloxy-3-arylpropylamines 1 and their optically pure enantiomers have been carried out using methods such as, for example, the methods disclosed in: U.S. Pat. No. 4,314,081; U.S. Pat. No. 5,068,432; *Tetrahedron Lett.* 30, 5207-5210 (1989); and *Tetrahedron*, 53, 6739-6746 (1997).

Surprisingly, we have discovered that aromatic displacement of 3-hydroxy-3-arylpropylamines 2 can be carried out with aryl halides, including unactivated aryl halides such as 2-methylphenyl halides and 2-methoxyphenyl halides, in the presence of a suitable catalyst and a base or mixture of bases. When using this method, the 3-aryloxy-3-arylpropylamine product (1) is obtained in high chemical yield and of excellent purity. Also, when optically enriched 3-hydroxy-3-arylpropylamines (2) are used, the process produces optically enriched 3-aryloxy-3-arylpropylamines (1). In other words, the stereochemical integrity of the chiral center is maintained. For this reason, this method is particularly useful for the preparation of optically enriched 3-aryloxy-3-arypropylamines such as atomoxetine.

Compound 2 can be obtained using the process disclosed in the present invention or the methods previously described in the art, for example, the methods disclosed in: *Tetrahedron Lett.*, 30, 5207-5210 (1989); *Tetrahedron*, 57, 7785-7811 (2001); U.S. Pat. Nos. 6,686,505; 6,008,412; and 4,324,081; *Adv. Synth. Catal.* 345, 261-274 (2003); *Tetrahedron Lett.* 43, 5435-36 (2002); *Tetrahedron: Asym.* 13, 2039-51 (2002); *Synth. Commun.* 25, 1231-38 (1995); *Tetrahedron Lett.* 35, 1339-1342 (1994); *Indian J. Chem.* 31B, 803-809 (1992); and *J. Org. Chem.* 52, 4081-4084 (1988).

According to an aspect of the present invention, the etherification of compound 2 with aryl halide 6 is carried out in the presence of a suitable catalyst and a base or a mixture of bases. The suitable catalysts include copper, palladium and nickel containing catalysts, of which copper-containing catalysts are preferred. More preferably, the copper-containing catalyst is selected from cupric chloride, cupric bromide, cupric iodide, cupric sulfate, cupric acetate, cupric triflate, cuprous chloride, cuprous bromide, cuprous iodide, cuprous acetate, cuprous triflate, copper (I) oxide, copper (II) oxide, and copper-zinc alloy. Suitable bases for this transformation include organic and inorganic bases, of which potassium carbonate, sodium carbonate, lithium carbonate, cesium carbonate, calcium carbonate, magnesium carbonate, magnesium oxide, sodium bicarbonate, potassium bicarbonate, lithium bicarbonate, cesium bicarbonate, their mixture thereof, and the like are preferred.

The reaction may be carried out in the absence or presence of an organic solvent or a mixture of solvents. Suitable solvents includes aliphatic and aromatic hydrocarbons such as heptanes, octanes, toluene, and xylenes; nitriles such as acetonitrile, propionitrile, butyronitrile, and benzonitrile; N,N-dialkylamides such as N,N-dimethylformamide, N,N-dimethylacetamide, and N-methyl-2-pyrrolidinone; cyclic and acyclic alkyl sulfoxides and sulfones such as dimethyl sulfoxide and sulfolane; aliphatic and aromatic ethers such as dibutyl ether, diphenyl ether, and anisole; and halogenated hydrocarbons such as dichloromethane and dichloroethane; of which hydrocarbons such as heptanes, octanes, toluene, and xylenes; and nitriles such as acetonitrile, propionitrile, butyronitrile, and benzonitrile are preferred.

The reaction may be carried out at temperatures of from about 0° C. to about 200° C., with temperatures of about 50° C. to 150° C. being preferred, and temperatures from 90° C. to 140° C. being more preferred. The product can be isolated and purified by techniques well known in the art, such as filtration, extraction, evaporation, trituration, and crystallization. The reaction yield ranges from 20% to 99%, typically from 60% to 95%.

Thus according to another aspect of the invention, a process is provided for the preparation of 3-aryloxy-3-arylpropylamines of formula 1,

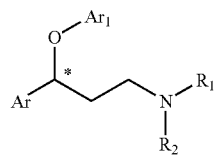

1 wherein Ar is an aryl group, of which phenyl and 2-thienyl are preferred; $Ar_1$ is an aryl group, of which 1-naphthyl, 2-methylphenyl, 2-methoxyphenyl, and 4-trifluoromethylphenyl are preferred; $R_1$ and $R_2$ individually represent hydrogen, C1-C10 alkyl, phenyl, and benzyl groups; the carbon center marked with "*" can be racemic or enantiomerically enriched (R)— or (S)— configuration; including fluoxetine, tomoxetine, nisoxetine, norfluoxetine, duloxetine and their optically enriched (R)- and (S)-enantiomers, and pharmaceutically acceptable addition salts thereof comprising the steps of:

(1) reacting compounds of formula 3,

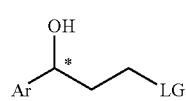

3 wherein Ar and "*" are as defined above; LG is a leaving group selected from halogens such as chloro, bromo, and iodo and sulfonate esters such as mesylate and p-tosylate, with an amine of formula $R_1R_2NH$ (4), wherein $R_1$ and $R_2$ are as defined above, and purifying and isolating the coupled product as its oxalic acid salt of formula 5,

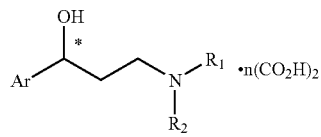

5 wherein Ar, $R_1$, $R_2$, and "*" are as defined above and n is 0.5 or 1;

(2) treating the salt 5 with a base to produce 3-hydroxy-3-arylpropylamines of formula 2,

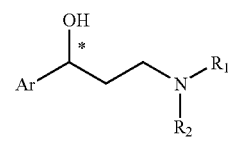

2 wherein Ar, $R_1$, $R_2$, and "*" are as defined above;

(3) reacting compounds of formula 2 with an aryl halide of formula $Ar_1X$ (6), wherein $Ar_1$ is an aryl group, of which 1-naphthyl, 2-methylphenyl, 2-methoxyphenyl, and 4-trifluoromethylphenyl are preferred; X is selected from halogens such as fluoro, chloro, bromo, and iodo, of which iodo is preferred, in the presence of a suitable catalyst and a base or mixture of bases to produce 3-aryloxy-3-arylpropylamines of formula 1; and (4) optional formation of an acid addition salt using a pharmaceutically acceptable acid.

Further, according to an aspect of the present invention, a process is provided for the preparing fluoxetine, tomoxetine, and nisoxetine and their optically enriched (R)- and (S)-enantiomers, and pharmaceutically acceptable addition salts thereof comprising the steps of:

(1) reacting compounds of formula 7,

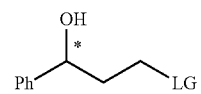

7 wherein LG is a leaving group selected from halogens such as chloro, bromo, and iodo and sulfonate esters such as mesylate and p-tosylate; with methylamine and isolating the resulting crude N-methyl-3-hydroxy-3-phenylpropylamine followed by treatment with oxalic acid to form the oxalate salt compound of formula 8,

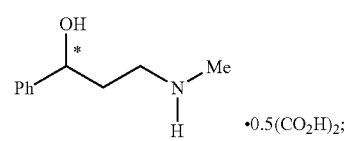

8

(2) treating the salt 8 with a base to produce N-methyl-3-hydroxy-3-phenylpropylamine 9;

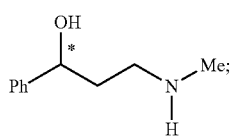

(3) reacting compound 9 with aryl halide Ar₁X (6), wherein Ar₁ is 2-methylphenyl, 2-methoxyphenyl or 4-trifluoromethylphenyl; X is selected from halogens such as fluoro, chloro, bromo, and iodo, of which iodo is preferred, in the presence of a suitable catalyst and a base or mixture of bases to produce fluoxetine, tomoxetine, or nisoxetine or their (R)- or (S)-enantiomer; and (4) optional formation of an acid addition salt using a pharmaceutically acceptable acid.

The 3-aryloxy-3-arylpropylamines described herein form pharmaceutically acceptable acid addition salts with a wide variety of organic and inorganic acids.

The present preparation of 3-aryloxy-3-arylpropylamines is carried out according to reaction Scheme 2 below where all substituents are as previously defined.

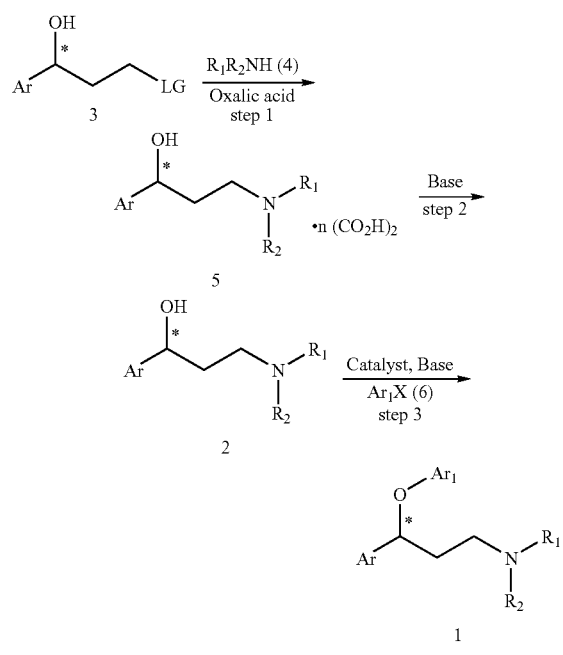

The etherification of compounds of formula 2 with aryl halides of formula 6 may be carried out in the presence of a suitable catalyst and a base or a mixture of bases. The suitable catalysts include copper, palladium and nickel containing catalysts, of which copper-containing catalysts are preferred. More preferably, the copper-containing catalyst is selected from cupric chloride, cupric bromide, cupric iodide, cupric sulfate, cupric acetate, cupric triflate, cuprous chloride, cuprous bromide, cuprous iodide, cuprous acetate, cuprous triflate, copper (I) oxide, copper (II) oxide, and copper-zinc alloy. Suitable bases for this transformation include organic and inorganic bases, of which potassium carbonate, sodium carbonate, lithium carbonate, cesium carbonate, calcium carbonate, magnesium carbonate, magnesium oxide, sodium bicarbonate, potassium bicarbonate, lithium bicarbonate, cesium bicarbonate, and their mixture thereof, and the like are preferred.

The reaction may be carried out in the absence or presence of an organic solvent or a mixture of solvents. The suitable solvents includes aliphatic and aromatic hydrocarbons such as heptanes, octanes, toluene, and xylenes; nitriles such as acetonitrile, propionitrile, butyronitrile, and benzonitrile; N,N-dialkylamides such as N,N-dimethylformamide, N,N-dimethylacetamide and N-methyl-2-pyrrolidinone; cyclic and acyclic alkyl sulfoxides and sulfones such as dimethyl sulfoxide and sulfolane; aliphatic and aromatic ethers such as dibutyl ether, diphenyl ether, and anisole; and halogenated hydrocarbons such as dichloromethane and dichloroethane; of which hydrocarbons such as heptanes, octanes, toluene, and xylenes; and nitriles such as acetonitrile, propionitrile, butyronitrile, and benzonitrile are preferred.

The reaction may be carried out at temperatures of from about 0° C. to about 200° C., with temperatures of about 50° C. to 150° C. being preferred, and temperatures from 90° C. to 140° C. being more preferred. The product can be isolated and purified by techniques well known in the art, such as filtration, extraction, evaporation, trituration, and crystallization. The reaction yields range from 20% to 99%, typically from 60% to 95%.

The present invention relates to processes for the preparation of 3-aryloxy-3-arylpropylamines 1, which include tertiary amines, secondary amines, and primary amines ($R_1=R_2=H$). It is understood by the skilled person that the amine moiety of these compounds can be modified by the methods known in the art to produce desired target compounds. For example, N,N-dimethylamines or N,N-methylbenzylamines can undergo mono-N-demethylation or debenzylation to form the N-methylamine compounds such as fluoxetine, tomoxetine, nisoxetine, and duloxetine as shown in Scheme 3. Similarly, primary amines can be converted to N-methylamine compounds such as fluoxetine, tomoxetine, nisoxetine, and duloxetine by N-methylation (Scheme 4) and N-benzyl amines can be converted to primary amines such as norfluoxetine by debenzylation (Scheme 5).

Scheme 3

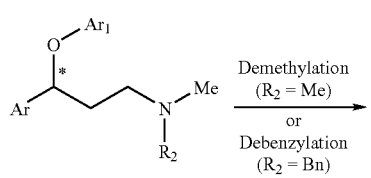

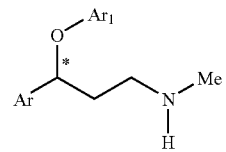

Scheme 4

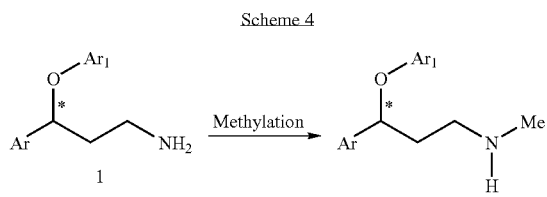

Scheme 5

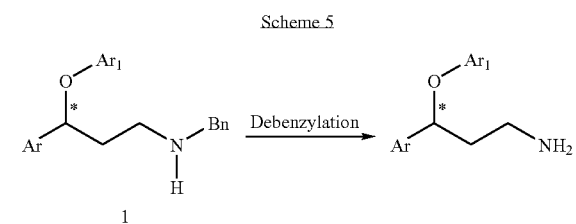

The processes of the instant invention are capable of preparing both enantiomerically enriched (R)- and (S)-stereoisomers and racemic mixtures of 3-aryloxy-3-arylpropylamines 1. It is also understood by the skilled person that the specific enantiomerically enriched stereoisomers may be obtained by resolution of the racemic product, intermediates, or in some cases the starting materials. Thus, when racemic mixtures of 3-aryloxy-3-arylpropylamines 1 are produced using the present processes, the product can be resolved into their specific isomers; namely, the (R)- or (S)-enantiomer.

Overall using the processes of the instant invention, a convenient and high-yielding method for the preparation of 3-aryloxy-3-arylpropylamines is achieved. Furthermore and of similar importance, these processes are highly stereospecific and yield pure material, thus providing 3-aryloxy-3-arylpropylamines of suitable quality for their use as pharmaceuticals.

The following non-limiting examples further illustrate the manner of carrying out the inventive process described herein.

EXAMPLE 1

A solution of (R)-3-chloro-1-phenylpropanol (1.0 g, 5.85 mmol) and a catalytic amount of sodium iodide in ethanol (7 mL) and 40% methylamine aqueous solution (15 mL) was stirred at 60° C. for 7 hours. The reaction mixture was evaporated to 3 mL, and the pH of the solution was adjusted to pH>12 via the addition of aqueous NaOH solution. The mixture was then extracted with toluene twice and the combined extracts were washed with brine. The toluene layer was evaporated to dryness and the residue dissolved in toluene (5 mL) and isopropanol (5.mL) and oxalic acid dihydrate (0.4 g, 3.2 mmol) was added. It was stirred at room temperature for 2Hours and the suspension was filtered and rinsed with toluene/isopropanol to provide 0.9 g of (R)—N-methyl-3-hydroxy-3-phenylpropylamine hemioxalate salt as an off-white solid. $^1$H NMR (D$_2$O) δ 7.5-7.2 (m, 5H), 4.8 (at, J=6.6 Hz, 1H), 5.15-2.9 (m, 2H), 2.64 (s, 3H), 2.2-2.0 (m, 2H). Elemental Analysis for $C_{11}H_{16}NO_3$; Calculated: H 7.67%; C 62.84%; N 6.66%.

Found: H 7.45%; C 62.57%; N 6.48%. The solid (0.85 g) was free based with sodium hydroxide solution and extracted with toluene. The extracts were washed with brine and then evaporated to dryness to give 0.62 g of (R)—N-methyl-3-hydroxy-3-phenylpropylamine as an off-white solid $[α]D^{23}=37°$ (c 1, CHCl$_3$). $^1$H NMR (CDCl$_3$) δ 7.4-7.2 (m, 5H), 4.96 (dd, J=8.6, 3.1 Hz, 1H), 3.0-2.8 (m, 2H), 2.46 (s, 3H), 1.9-1.7 (m, 2H).

EXAMPLE 2

A solution of (R)-3-iodo-1-phenylpropanol (5.0 g, 19 mmol) and catalytic amount of sodium iodide in tetrahydrofuran (20 mL) and 40% aqueous methylamine (40 mL) was stirred at room temperature for 5 hours. The reaction mixture was evaporated to 15 mL and the pH of the solution was adjusted to pH>12 via the addition of aqueous NaOH solution. The mixture was then twice extracted with toluene and the combined extracts were washed with brine. The toluene layer was evaporated to dryness and the residue dissolved in toluene (25 mL) and isopropanol (25 mL) and oxalic acid dihydrate (1.2 g, 9.5 mmol) was added and the mixture was stirred at room temperature for 2 hours. The resulting suspension was filtered and rinsed with toluene/isopropanol to give 3.0 g of (R)—N-methyl-3-hydroxy-3-phenylpropylamine hemioxalate salt as an off-white solid. The solid (2.9 g) was free based with sodium hydroxide solution and extracted with toluene. The extracts were washed with brine and then evaporated to dryness to give 2.2 g of (R)—N-methyl-3-hydroxy-3-phenylpropylamine as an off-white solid $[α]D^{23}=36°$ (c 1, CHCl$_3$).

EXAMPLE 3

A mixture of (R)—N-methyl-3-hydroxy-3-phenylpropylamine (0.33 g, 2 mmol), 4-iodobenzotrifluoride (0.82 g, 3 mmol), cuprous iodide (0.1 g), cesium carbonate (1.3 g, 4 mmol) and butyronitrile (0.5 mL) was stirred under nitrogen at 130-140° C. until reaction completion as determined by $^1$H NMR (16-24 hours). The reaction mixture was cooled to room temperature, diluted with methyl t-butyl ether (10 mL), filtered, and rinsed with more methyl t-butyl ether. A 20% HCl solution in isopropanol (1 mL) was added and the resulting solution was evaporated to dryness to give a solid residue. The residue was stirred with methyl t-butyl ether (5 mL) for 1Hour at room temperature and the suspension was filtered and washed with more methyl t-butyl ether to give 0.59 g of (R)—N-methyl-3-(4-trifluoromethylphenoxy)-3-phenylpropylamine hydrochloride ((R)-Fluoxetine hydrochloride) as a white solid $[α]D^{23}=−16.1°$ (c 1, CHCl$_3$). $^1$H NMR (CDCl$_3$) δ 9.73 (br s, 2H), 7.42 (d, J=8.7 Hz, 2H), 7.4-7.2 (m, 5H), 6.91 (d, J=8.7 Hz, 2H), 5.48 (dd, J=8.0, 4.5 Hz, 1H), 3.2-3.0 (m, 2H), 2.63 (at, J=5.4 Hz, 3H), 2.6-2.4 (m, 2H).

EXAMPLE 4

A mixture of N-methyl-3-hydroxy-3-phenylpropylamine (1.65 g, 10 mmol), 4-iodobenzotrifluoride (3.25 g, 12 mmol), cuprous bromide (0.17 g), cesium carbonate (3.9 g, 12 mmol) and xylenes (1 mL) was stirred under nitrogen at 130° C. until reaction completion as determined by $^1$H NMR (16 hours). The reaction mixture was cooled to room temperature, diluted with methyl t-butyl ether (20 mL), filtered, and rinsed with more methyl t-butyl ether. 20% HCl solution in isopropanol (3 mL) was added and the resulting solution was evaporated to dryness to yield a solid residue. The residue was stirred with methyl t-butyl ether (20 mL) for 1Hour at room temperature and the suspension was filtered and washed with more methyl t-butyl ether to give 2.4 g of N-methyl-3-(4-trifluoromethylphenoxy)-3-phenylpropylamine hydrochloride (Fluoxetine hydrochloride) as a white solid. $^1$H NMR spectrum of the product is identical to that of Example 3.

EXAMPLE 5

A mixture of (R)—N-methyl-3-hydroxy-3-phenylpropylamine (0.33 g, 2 mmol), 2-iodotoluene (0.65 g, 3 mmol), cuprous iodide (0.1 g), cesium carbonate (1.3 g, 4 mmol) and xylenes (1.2 mL) was stirred under nitrogen at 130° C. until reaction completion as assessed by $^1$H NMR. The reaction mixture was cooled to room temperature, diluted with methyl t-butyl ether (10 mL), filtered, and rinsed with more methyl t-butyl ether. A 20% HCl solution in isopropanol (1 mL) was added and the resulted suspension stirred at 0-5° C. and filtered and washed with more methyl t-butyl ether to give 0.48 g of (R)—N-methyl-3-(2-methylphenoxy)-3-phenylpropylamine hydrochloride (Atomoxetine hydrochloride) as an off-white solid $[\alpha]D^{23}=-41°$ (c 1, Methanol). $^1$H NMR (CDCl$_3$) δ 9.7 (br s, 2H), 7.4-7.2 (m, 5H), 7.1 (d, J=7.5 Hz, 1H), 6.95 (dd, J=8.1, 7.0 Hz, 1H), 6.78 (dd, J=7.5, 7.0 Hz, 1H), 6.6 (d, J=8.1 Hz, 1H), 5.38 (dd, J=7.9, 4.5 Hz, 1H), 3.14 (t, J=7.7 Hz, 2H), 2.61 (s, 3H), 2.6-2.4 (m, 2H), 2.30 (s, 3H).

EXAMPLE 6

A mixture of (R)—N-methyl-3-hydroxy-3-phenylpropylamine (0.3 g, 1.8 mmol), 2-iodotoluene (0.59 g, 2.7 mmol), cuprous iodide (0.1 g), potassium carbonate (0.14 g, 1 mmol) and xylenes (1 mL) was stirred under nitrogen at 130° C. until reaction completion as determined by $^1$H NMR. The reaction mixture was cooled to room temperature and washed with saturated aqueous potassium carbonate and water. The organic layer was twice extracted with dilute hydrochloric acid solution. The combined aqueous layers were adjusted to pH>10 via the addition of NaOH solution and extracted with methyl t-butyl ether. The combined extracts were washed with an aqueous EDTA (0.1g) solution (3 mL) and additional water. The organic layer was evaporated to dryness and the residue dissolved in ethyl acetate (10 mL). A 20% HCl solution in isopropanol (1 mL) was added and the resulting suspension stirred at 0-5° C., filtered, and washed with more ethyl acetate to give 0.3 g of (R)—N-methyl-3-(2-methylphenoxy)-3-phenylpropylamine hydrochloride (Atomoxetine hydrochloride) as an off-white solid $[\alpha]D^{23}=-40°$ (c 1, Methanol). $^1$H NMR spectrum of the product is identical to that of Example 5.

EXAMPLE 7

A mixture of N-methyl-3-hydroxy-3-phenylpropylamine (0.3 g, 1.8 mmol), 2-iodotoluene (0.59 g, 2.7 mmol), cupric sulfate (0.06 g), cesium carbonate (0.65 g, 2.0 mmol) and xylenes (0.5 mL) was stirred under nitrogen at 130-140° C. until reaction completion as determined by $^1$H NMR. The reaction mixture was cooled to room temperature and filtered, washed with toluene. The filtrate was washed with 5% aqueous ammonia solution and water. The organic layer was evaporated to dryness and the residue dissolved in ethyl acetate (5 mL). A 20% HCl solution in isopropanol (0.5 g) was added and the resulting suspension stirred at 0-5° C., filtered, and washed with more ethyl acetate to give 0.22 g of N-methyl-3-(2-methylphenoxy)-3-phenylpropylamine hydrochloride (Tomoxetine hydrochloride) as an off-white solid. $^1$H NMR spectrum of the product is identical to that of Example 5.

EXAMPLE 8

A mixture of N,N-dimethyl-3-hydroxy-3-phenylpropylamine (0.9 g, 5 mmol), 2-iodotoluene (1.31 g, 6 mmol), cuprous iodide (0.2 g) and cesium carbonate (1.8 g, 5.5 mmol) was stirred under nitrogen at 130° C. until the reaction was complete as determined by $^1$H NMR. The reaction mixture was cooled to room temperature, diluted with methyl t-butyl ether (10 mL), filtered, and rinsed with more methyl t-butyl ether. The filtrate was extracted with diluted hydrochloric acid solution and the aqueous layer was washed with more methyl t-butyl ether. The aqueous was adjusted to pH>10 by the addition of sodium hydroxide solution, then extracted with methyl t-butyl ether twice. The combined extracts were washed with water and then evaporated to dryness to give 1.2 g of N,N-dimethyl-3-(2-methylphenoxy)-3-phenylpropylamine as a light yellow oil. $^1$H NMR (CDCl$_3$) δ 7.45-7.2 (m, 5H), 7.12 (d, J=6.8 Hz, 1H), 7.0 (dd, J=8.0, 7.6 Hz, 1H), 6.78 (dd, J=8.4, 6.8 Hz, 1H), 6.63 (d, J=8.1 Hz, 1H), 5.24 (dd, J=8.1, 4.8 Hz, 1H), 2.46 (t, J=7.3 Hz, 2H), 2.33 (s, 3H), 2.24 (s, 6H), 2.3-2.1 (m, 1H), 2.05-1.9 (m, 1H).

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

What is claimed is:

1. A process for the preparation of compounds including the optically enriched (R)- and (S)-enantiomers of the compounds, and pharmaceutically acceptable addition salts thereof, comprising the steps of reacting compounds of formula 2,

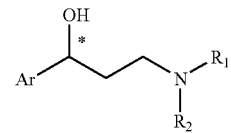

wherein Ar is an aryl group; the carbon center marked with "*" can be racemic or enantiomerically enriched having the (R) — or (S ) — configuration; R$_1$ and R$_2$ individually represent hydrogen, C1-C10 alkyl, aryl, and aralkyl groups; with an aryl halide of formula Ar$_1$X (6), wherein Ar$_1$ is an awl group and X is a halogen, in the presence of a suitable copper containing catalysts and a base or mixture of bases to produce a 3-aryloxy-3-arylpropylamine of formula 1:

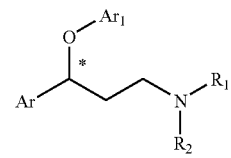

wherein Ar, Ar$_1$, R$_1$, R$_2$, and "*" are as defined above.

2. The process according to claim 1, wherein Ar is phenyl or 2-thienyl.

3. The process according to claim 1, wherein $Ar_1$ is selected from 1-naphthyl 2-methylphenyl, 2-methoxyphenyl, and 4-trifluoromethylphenyl.

4. The process according to claim 1, wherein X is selected from fluorine, chlorine, bromine and iodine.

5. The process according to claim 1, wherein X is iodine.

6. A process according to claim 1 wherein the catalyst is selected from cupric chloride, cupric bromide, cupric iodide, cupric sulfate, cupric acetate, cupric triflate, cuprous chloride, cuprous bromide, cuprous iodide, cuprous acetate, cuprous triflate, copper (I) oxide, copper (II) oxide, and copper-zinc alloy.

7. The process according to claim 1 wherein the bases are selected from organic and inorganic bases.

8. The process according to claim 1 wherein the base is selected from potassium carbonate, sodium carbonate, lithium carbonate, cesium carbonate, calcium carbonate, magnesium carbonate, magnesium oxide, sodium bicarbonate, potassium bicarbonate, lithium bicarbonate, cesium bicarbonate, their mixture thereof, and the like.

9. A process according to claim 1 wherein the compound is N-methyl-3-(4-trifluoromethylphenoxy)-3-phenylpropylamine (Fluoxetine) and its pharmaceutically acceptable salts.

10. A process according to claim 1 wherein the compound is (R)—N-methyl-3-(4-trifluoromethylphenoxy)-3-phenylpropylamine and its pharmaceutically acceptable salts.

11. A process according to claim 1 wherein the compound is (S)—N-methyl-3-(4-trifluoromethylphenoxy)-3-phenylpropylamine and its pharmaceutically acceptable salts.

12. A process according to claim 1 wherein the compound is N-methyl-3-(2-methylphenoxy)-3-phenylpropylamine (Tomoxetine) and its pharmaceutically acceptable salts.

13. A process according to claim 1 wherein the compound is (R)—N-methyl-3-(2-methylphenoxy)-3-phenylpropylamine (Atomoxetine) and its pharmaceutically acceptable salts.

14. A process according to claim 1 wherein the compound is (S)—N-methyl-3-(2-methylphenoxy)-3-phenylpropylamine and its pharmaceutically acceptable salts.

15. A process according to claim 1 wherein the compound is N-methyl-3-(2-methoxyphenoxy)-3-phenylpropylamine (Nisoxetine) and its pharmaceutically acceptable salts.

16. A process according to claim 1 wherein the compound is (R)—N-methyl-3-(2-methoxyphenoxy)-3-phenylpropylamine and its pharmaceutically acceptable salts.

17. A process according to claim 1 wherein the compound is (S)—N-methyl-3-(2-methoxyphenoxy)-3-phenylpropylamine and its pharmaceutically acceptable salts.

18. A process according to claim 1 wherein the compound is N-methyl-3-(1-naphthoxy)-3-(2-thienyl)propylamine and its pharmaceutically acceptable salts.

19. A process according to claim 1 wherein the compound is (R)—N-methyl-3-(1-naphthoxy)-3-(2-thienyl)propylamine and its pharmaceutically acceptable salts.

20. A process according to claim 1 wherein the compound is (S)—N-methyl-3-(1-naphthoxy)-3-(2-thienyl)propylamine and its pharmaceutically acceptable salts.

21. A process according to claim 1 wherein the compound is 3-(4-trifluoromethylphenoxy)-3-phenylpropylamine (Norfluoxetine) and its pharmaceutically acceptable salts.

22. A process according to claim 1 wherein the compound is (R)-3-(4-trifluoromethylphenoxy)-3-phenylpropylamine and its pharmaceutically acceptable salts.

23. A process according to claim 1 wherein the compound is (S)-3-(4-trifluoromethylphenoxy)-3-phenylpropylamine and its pharmaceutically acceptable salts.

24. The process for the preparation of compounds including the optically enriched (R)- and (S)-enantiomers of the compounds, and pharmaceutically acceptable addition salts thereof, comprising the steps of:

i) reacting compounds of formula 3,

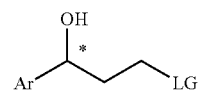

wherein Ar is an aryl group; the carbon center marked with "*" can be racemic or enantiomerically enriched having the (R)— or (S)— configuration; and LG is a leaving group, with an amine of formula $R_1R_2NH$ (4), wherein $R_1$ and $R_2$ individually represent hydrogen, C1-C10 alkyl, aryl, and aralkyl groups, and isolating the hemioxalic acid salt of the coupled product of formula 5,

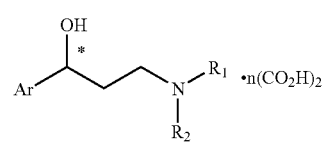

wherein Ar, $R_1$, $R_2$, and "*" are as defined above and n is 0.5;

ii) treating the salt 5 with a base or basic ion-exchange resin to produce 3-hydroxy-3-arylpropylamines of formula 2,

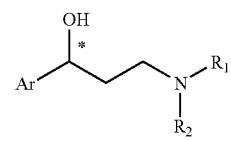

wherein Ar, $R_1$, $R_2$, and "*" are as defined above;

iii) reacting compounds of formula 2 with aryl halides of formula $Ar_1X$ (6), wherein $Ar_1$ is an aryl group and X is a halogen, in the presence of a suitable copper-containing catalyst and a base or mixture of bases to produce the 3 aryloxy-3-arylpropylamine of formula 1,

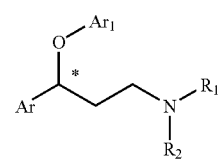

wherein Ar, $Ar_1$, $R_1$, $R_2$ and "*" are as defined above; and their pharmaceutically acceptable addition salts thereof; and iv) optional formation of an acid addition salt using a pharmaceutically acceptable acid.

25. The process according to claim 24 where Ar is phenyl or 2-thienyl.

26. The process according to claim 24 wherein LG is selected from halogens such as chlorine, bromine, iodine, and sulfonate esters such as mesylate and p-tosylate.

27. The process according to claim 24 wherein the suitable solvents for hemioxalic acid salt formation are selected from alcohols, alkyl ethers, alkyl esters, ketones, aliphatic and aromatic hydrocarbons, halogenated hydrocarbons and mixtures thereof.

28. The process according to claim 24 wherein the solvent for oxalic acid salt formation is selected from methanol, ethanol, isopropanol, n-propanol, butanol, diethyl ether, methyl t-butyl ether, diisopropyl ether, butyl ether, ethyl acetate, hexanes, heptanes, dichloromethane, dichloroethane, toluene, xylenes, acetone, methyl ethyl ketone, and methyl isobutyl ketone and mixtures thereof.

29. The process according to claim 24 wherein $Ar_1$ is selected from 1-naphthyl, 2-methylphenyl 2-methoxyphenyl, and 4-trifluoromethylphenyl.

30. The process according to claim 24, wherein X is selected from fluorine, chlorine, bromine and iodine.

31. The process according to claim 24, wherein X is iodine.

32. A process according to claim 24 wherein the catalyst is selected from cupric chloride, cupric bromide, cupric iodide, cupric sulfate, cupric acetate, cupric triflate, cuprous chloride, cuprous bromide, cuprous iodide, cuprous acetate, cuprous triflate, copper (I) oxide, copper (II) oxide, and copper-zinc alloy.

33. The process according to claim 24 wherein the bases are selected from organic and inorganic bases.

34. The process according to claim 24 wherein the base is selected from potassium carbonate, sodium carbonate, lithium carbonate, cesium carbonate, calcium carbonate, magnesium carbonate, magnesium oxide, sodium bicarbonate, potassium bicarbonate, lithium bicarbonate, cesium bicarbonate, their mixture thereof, and the like.

35. A process according to claim 24 wherein the compound is N-methyl-3-(4-trifluoromethylphenoxy)-3-phenylpropylamine (Fluoxetine) and its pharmaceutically acceptable salts.

36. A process according to claim 24 wherein the compound is (R)—N-methyl-3-(4-trifluoromethylphenoxy)-3-phenyl-propylamine and its pharmaceutically acceptable salts.

37. A process according to claim 24 wherein the compound is (S)—N-methyl-3-(4-trifluoromethylphenoxy)-3-phenyl-propylamine and its pharmaceutically acceptable salts.

38. A process according to claim 24 wherein the compound is N-methyl-3-(2-methylphenoxy)-3-phenylpropylamine (Tomoxetine) and its pharmaceutically acceptable salts.

39. A process according to claim 24 wherein the compound is (R)—N-methyl-3-(2-methylphenoxy)-3-phenylpropylamnine (Atomoxetine) and its pharmaceutically acceptable salts.

40. A process according to claim 24 wherein the compound is (S)—N-methyl-3-(2-methylphenoxy)-3-phenylpropylamine and its pharmaceutically acceptable salts.

41. A process according to claim 24 wherein the compound is N-methyl-3-(2-methoxyphenoxy)-3-phenylpropylamine (Nisoxetine) and its pharmaceutically acceptable salts.

42. A process according to claim 24 wherein the compound is (R)—N-methyl-3-(2-methoxyphenoxy)-3-phenylpropy-lamine and its pharmaceutically acceptable salts.

43. A process according to claim 24 wherein the compound is (S)—N-methyl-3-(2-methoxyphenoxy)-3-phenylpropy-lamine and its pharmaceutically acceptable salts.

44. A process according to claim 24 wherein the compound is N-methyl-3-(1-naphthoxy)-3-(2-thienyl)propylamine and its pharmaceutically acceptable salts.

45. A process according to claim 24 wherein the compound is (R)—N-methyl-3-(1-naphthoxy)-3-(2-thienyl)propy-lamine and its pharmaceutically acceptable salts.

46. A process according to claim 24 wherein the compound is (S)—N-methyl-3-(1-naphthoxy)-3-(2-thienyl)propy-lamine and its pharmaceutically acceptable salts.

47. A process according to claim 24 wherein the compound is 3-(4-trifluoromethylphenoxy)-3-phenylpropylamine (Norfluoxetine) and its pharmaceutically acceptable salts.

48. A process according to claim 24 wherein the compound is (R)-3-(4-trifluoromethylphenoxy)-3-phenylpropylamine and its pharmaceutically acceptable salts.

49. A process according to claim 24 wherein the compound is (S)-3-(4-trifluoromethylphenoxy)-3-phenylpropylamine and its pharmaceutically acceptable salts.

* * * * *